(12) United States Patent
Tani et al.

(10) Patent No.: US 6,764,480 B2
(45) Date of Patent: Jul. 20, 2004

(54) DISPOSABLE DIAPER

(75) Inventors: Koichiro Tani, Kagawa-ken (JP); Toshiyasu Yoshioka, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 177 days.

(21) Appl. No.: 09/943,183

(22) Filed: Aug. 30, 2001

(65) Prior Publication Data

US 2002/0026173 A1 Feb. 28, 2002

(30) Foreign Application Priority Data

Aug. 31, 2000 (JP) ........................................ 2000-263371

(51) Int. Cl.[7] ............................................... A61F 13/15
(52) U.S. Cl. ................................................... 604/391
(58) Field of Search ........................... 604/385.01, 386, 604/389–391

(56) References Cited

U.S. PATENT DOCUMENTS

| | | | | |
|---|---|---|---|---|
| 5,108,384 A | * | 4/1992 | Goulait | ........................ 604/390 |
| 5,318,555 A | | 6/1994 | Siebers et al. | |
| 5,897,546 A | * | 4/1999 | Kido et al. | .................. 604/391 |
| 5,984,911 A | * | 11/1999 | Siebers et al. | ............... 604/391 |
| 6,387,085 B1 | * | 5/2002 | Van Gompel et al. | ...... 604/391 |
| 6,443,937 B1 | * | 9/2002 | Matsushita | ................... 604/391 |
| 6,454,753 B1 | * | 9/2002 | Shimoe et al. | .............. 604/391 |

FOREIGN PATENT DOCUMENTS

| | | |
|---|---|---|
| EP | 0 786 243 A2 | 7/1997 |
| JP | 9-191908 | 7/1997 |
| WO | WO 90/07313 | 7/1990 |
| WO | WO 95/25496 | 9/1995 |
| WO | WO 98/27921 | 7/1998 |

OTHER PUBLICATIONS

Copy of European Search Report dated Nov. 14, 2002.

* cited by examiner

Primary Examiner—John J. Calvert
Assistant Examiner—C. Lynne Anderson
(74) Attorney, Agent, or Firm—Butzel Long

(57) ABSTRACT

A disposable diaper that includes a pair of tape fasteners extending outward from transversely opposite side edge portions of a rear waist region and a target tape strip to which the tape fasteners are anchored and attached to a outer surface of a backsheet in a front waist region. Hook members are provided on surfaces of the respective tape fasteners facing the target tape strip. Portions of the respective hook members defined in the vicinity of their inner side edges and lying in the vicinity of the transversely opposite side edge portions of to rear waist region are set free from the respective tape fasteners.

3 Claims, 7 Drawing Sheets

DISPOSABLE DIAPER

BACKGROUND OF THE INVENTION

This invention relates to a disposable diaper for absorbing and containing excretion.

Japanese Patent Application Publication No. 1997-191908A describes an open-type disposable diaper basically comprising a liquid-pervious topsheet, a liquid-impervious backsheet and a liquid-absorbent core disposed between these two sheets and further comprising a pair of tape fasteners extending outward from transversely opposite side edge portions of a rear waist region in transverse direction and a target tape strip attached to outer surface of the backsheet in a front waist region. In this diaper of well known art, a loop member is used as the target tape strip and the respective tape fasteners are provided on their surfaces facing the target tape strip with hook members. The target tape strip serves as an anchoring zone for the tape fasteners. In this diaper of well known art, the hook members are engaged with the target tape strip and thereby the tape fasteners are fixed to the target tape strip so as to connect the front and rear waist regions to each other. A waist-opening and a pair of leg-openings are defined as the front and rear waist regions are connected together in this manner.

In the case of the diaper disclosed in the Publication, the transversely opposite side edge portions of the front and rear waist regions are moved as the legs of a wearer move and this movement is transmitted via the tape fasteners to the hook members. Depending on a degree of the diaper' movement, a peeling force and/or a shearing force tending to disengage the hook members from the target tape strip are exerted upon the hook member and the target tape strip. Such peeling force and shearing force is generally concentrated in the vicinity of inner side edges of the respective hook members lying in the vicinity of the transversely opposite side edge portions of the rear waist region and in the vicinity of the target tape strip's both side edges lying in the vicinity of the transversely opposite side edge portions of the front waist region.

In this diaper disclosed therein, the portions of the respective hook members defined in the vicinity of their inner side edges are bonded to the tape fasteners, so the portions of the hook member defined in the vicinity of their inner side edges are not freely movable under constraint by the tape fasteners. Consequently, the peeling force and shearing force are exerted directly upon the portions of the hook members defined in the vicinity of their inner side edges and the inner side edge portions of the hook members may be readily disengaged from the target tape strip.

Furthermore, the portions of the target tape strip defined in the vicinity of its both side edges are bonded to the backsheet, so these portions of the target tape strip are restrained by the diaper and not freely movable. As a result, if the portions of the hook members defined in the vicinity of their inner side edges come in engagement with the portions of the target tape strip defined in the vicinity of its both side edges, the peeling force and shearing force are exerted directly upon the portions of the hook members defined in the vicinity of their inner side edges as well as upon the portions of the target tape strip defined in the vicinity of its both side edges. With a consequence, the inner edge portions of the respective hook members may be easily disengaged from the target tape strip.

In the known diaper, disengagement between the hook members and the target tape strip rapidly proceeds as the inner side edges of the hook members are disengaged from the target tape strip until the hook members are completely disengaged from the target tape strip.

SUMMARY OF THE INVENTION

It is an object of this invention to provide a disposable diaper designed so that the hook members are not readily disengaged from the target tape strip even if the diaper moves after the front and rear waist regions have been connected to each other to put the diaper on a wearer's body.

According to this invention, there is provided a disposable diaper with mechanical comprising a liquid-pervious topsheet, a liquid-impervious backsheet and a liquid-absorbent core disposed between these top- and backsheets so as to define, in a longitudinal direction of the diaper, a front waist region, a rear waist region and a crotch region extending between these front and rear waist regions, a pair of tape fasteners being used to connect the front and rear waist regions to each other extend outward transversely opposite side edge portions of the rear waist region in a transverse direction and a target tape strip on which the tape fasteners are anchored being provided on an outer surface of the backsheet in the front waist region.

According to this invention one of a hook member and a loop member is provided on a surface of the tape fastener facing the target tape strip and a portion of the one member defined in vicinity of an inner edge of the one member and lying in vicinity of the associated side edge portion of the rear waist region is not bonded to the tape fastener but set free from the tape fastener; and the target tape strip is formed by the other of the hook member and the loop member.

According to one embodiment of this invention, portions of the target tape strip defined in vicinity of its both side edges and lying in vicinity of the transversely opposite side edge portions of the front waist region are not bonded to the backsheet but set free from the backsheet.

According to another embodiment of this invention, the target tape strip is bonded to the backsheet along a plurality of bonding zones spaced apart from one another by a predetermined dimension in the transverse direction and remaining zones defined between respective pairs of the adjacent bonding zones are not bonded to the backsheet but set free from the backsheet.

DETAILED DESCRIPTION OF THE PREFERRED EMBODIMENTS

Details of a disposable diaper according to this invention will be more fully understood from the description given hereunder with reference to the accompanying drawings.

Figure 1:
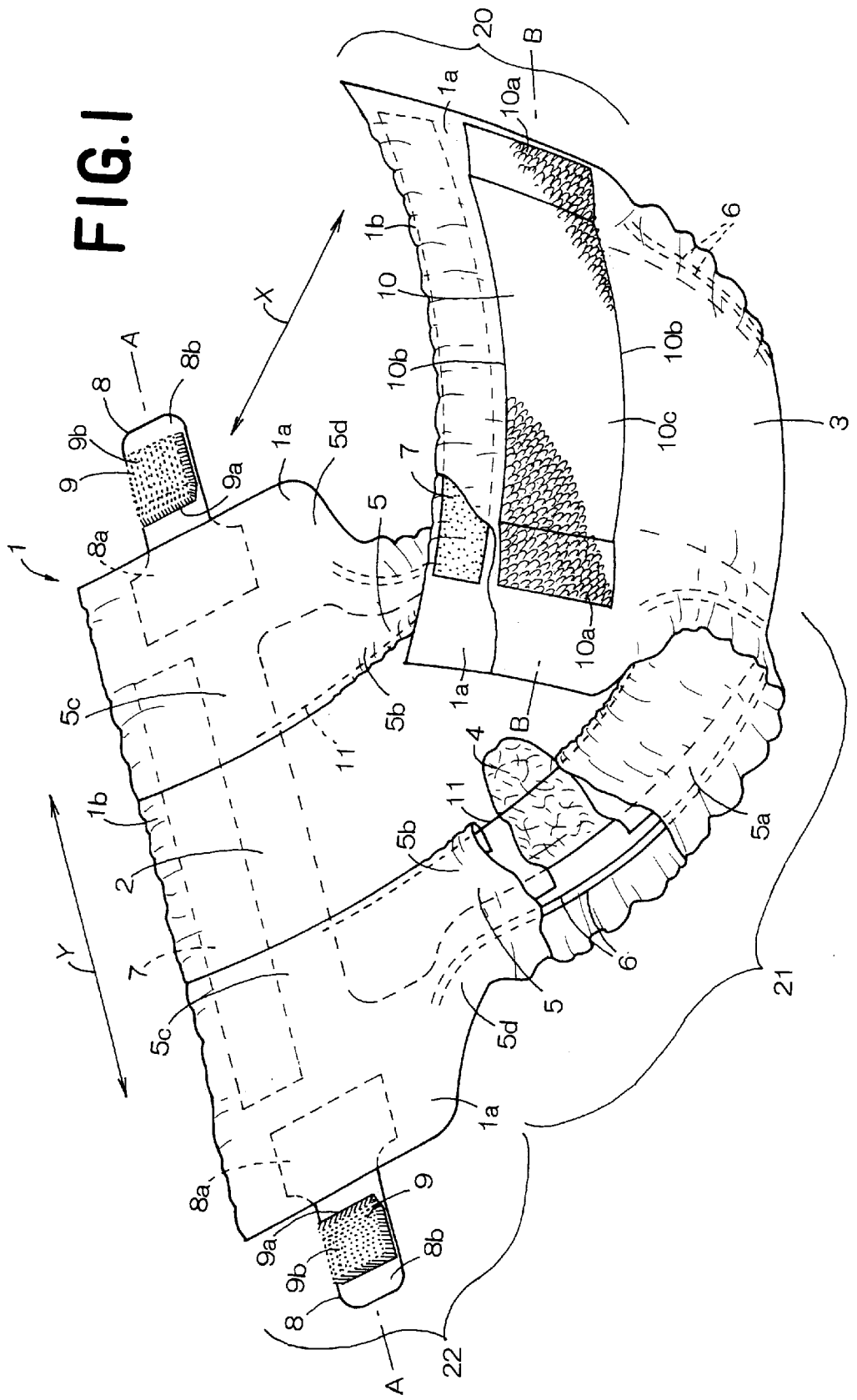
FIG. 1 is a perspective view showing a disposable diaper according to this invention as partially broken away.
Figure 2:
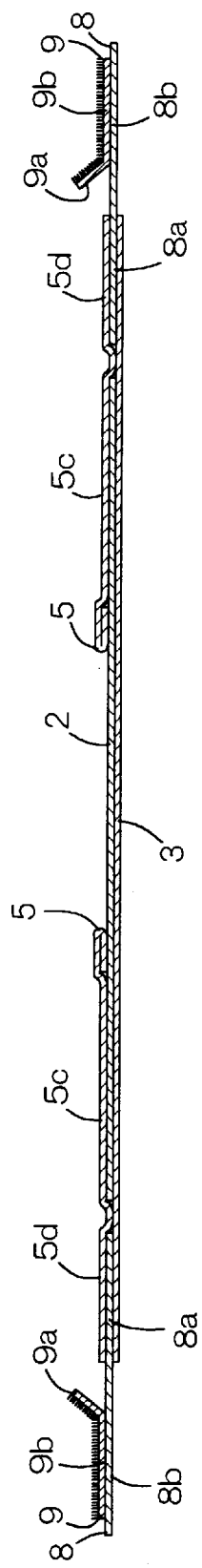
FIG. 2 is a sectional view taken along a line A—A in FIG. 1.
Figure 3:
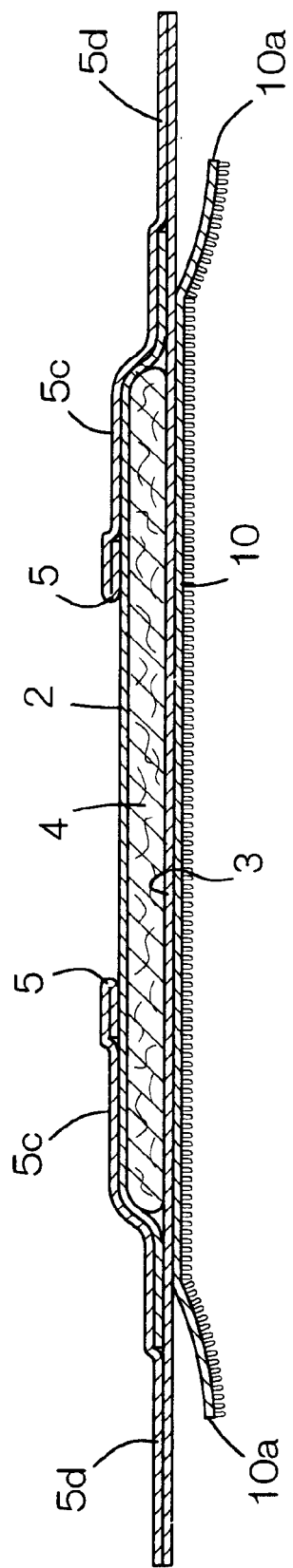
FIG. 3 is a sectional view taken along a line B—B in FIG. 1.

FIG. 1 is a perspective view showing a disposable diaper according to this invention as partially broken away, FIG. 2 a sectional view taken along a line A—A in FIG. 1 and FIG. 3 a sectional view taken along a line B—B in FIG. 1. Referring to FIG. 1, a longitudinal direction is indicated by an arrow X and a transverse direction is indicated by an arrow Y. Terms used herein as inner surfaces of various members such as top-and backsheets 2, 3 and leak-barrier sheets 5 should be understood to be the surfaces of these members facing a core 4 and terms "outer surfaces" thereof should be understood to be their surfaces not facing the core 4.

The diaper 1 basically comprises the liquid-pervious topsheet 2, the liquid-impervious backsheet 3 and the liquid-absorbent core 4 disposed between the top- and backsheets 2, 3 and entirely covered with and bonded to liquid-permeable sheet such as tissue paper (not shown). The core 4 is bonded to respective inner surfaces of the top- and backsheets 2, 3 by means of the liquid-permeable sheet.

In the longitudinal direction, the diaper 1 is composed of a front waist region 20, a rear waist region 22 and a crotch region 21 extending between the front and rear waist regions 20, 22. The diaper 1 has transversely opposite side edge portions 1a defined in the longitudinal direction and longitudinally opposite end portions 1b defined in the transverse direction. The side edge portions 1a curve inward in the transverse direction of the diaper 1 in the crotch region 21 so as to describe circular arcs, respectively.

The diaper 1 is provided along the side edge portions 1a with a pair of leak-barrier sheets 5, respectively, defined in the longitudinal direction. Elastic members 6 each comprising a plurality of elastic elements and being stretchable in the longitudinal direction are attached under tension to the diaper 1 along the side edge portions 1a thereof so as to be associated with respective leg-openings. Ribbon-like elastic members 7 being stretchable in the transverse direction are attached under tension to the diaper 1 along its longitudinally opposite end portions 1b so as to be associated with a waist-opening.

In the rear waist region 22 of the diaper 1, a pair of tape fasteners 8 extend outward from the opposite side edge portions 1a in the transverse direction, respectively. In the front waist region 20 of the diaper 1, a target or landing tape strip 10 on which the tape fasteners 8 are destined to be anchored is attached to the outer surface of the backsheet 3.

The tape fasteners 8 are formed with a flexible nonwoven fabric and have proximal end portions 8a and free end portions 8b extending outward from the respective proximal end portions 8a in the transverse direction. The surfaces of the respective free end portions 8b facing the target tape strip 10 are provided with hook members 9 having a plurality of hook elements, respectively. It is also possible to form the respective tape fasteners 8 from flexible plastic sheets.

The hook members 9 are substantially rectangular and inner edge portions of these hook members 9 lying adjacent the respective side edge portions of the rear waist region are not bonded to the respective tape fasteners 8 but set free from the tape fasteners 8. The remaining regions 9b of the hook members 9 except the inner edge portions 9a are bonded to the tape fasteners 8 by means of adhesive (not shown). Before the diaper 1 is actually worn, the free end portions 8b of the tape fasteners 8 remain folded onto the outer surface of the topsheet 2 and temporarily bonded to the topsheet 2 by means of the hook members 9 (not shown).

The target tape strip 10 is formed with a rectangular flexible loop member having a plurality of loop elements which is longer in the transverse direction, i.e., has transversely opposite side edges 10a extending in the longitudinal direction and longitudinally opposite ends 10b extending in the transverse direction. The portions of the target tape 10 in the vicinity of its side edges 10a are not bonded to the backsheet 3, i.e., set free from the backsheet 3. The remaining portion 10c of the target tape strip 10 except the portions in the vicinity of the side edges 10a is bonded to the outer surface of the backsheet 3 by means of adhesive (not shown).

Each of the leak-barrier sheets 5 has a fixed side edge portion 5a, a free side edge portion 5b and longitudinally opposite end portions 5c collapsed inward in the transverse direction of the diaper 1 so as to be placed upon the topsheet 2. The leak-barrier sheet 5 further has an outer side portion 5d extending outward from the fixed side edge portion 5a in the transverse direction of the diaper 1. The fixed side edge portion 5a and the longitudinally opposite ends 5c are bonded to the outer surface of the topsheet 2. A longitudinally stretchable elastic member 11 is bonded under tension to the free side edge portion 5b. The elastic member 11 is covered with a part of the free side edge portion 5b.

Along the transversely opposite edge portions 1a of the diaper 1, the topsheet 2 extends outward slightly beyond transversely side edges of the core 4 in the transverse direction. The backsheet 3 and the outer side portions 5d of the respective leak-barrier sheets 5 extend further outward beyond the respective side edges of the topsheet 2 in the transverse direction. Along the side edge portions 1a, portions of the top- and backsheets 2, 3 and the outer side portions 5d of the respective leak-barrier sheets 5 placed upon one another are bonded together. Along the longitudinally opposite end portions 1b of the diaper 1, the top- and backsheets 2, 3 extend outward beyond longitudinally opposite ends of the core 4 and portions of these top- and backsheets 2, 3 and leak-barrier sheets 5 placed upon one another are bonded together.

Each of the tape fasteners 8 has its proximal end portion 8a disposed between the top- and backsheets 2, 3 and bonded to respective inner surfaces of these sheets 2, 3 by means of adhesive (not shown). Each of the elastic members 6 associated with the leg-opening is disposed between the backsheet 3 and the outer side portion 5d of the leak-barrier sheet 5 and bonded to respective inner surfaces of these sheets 3, 5. The elastic member 7 associated with the waist-opening is disposed between the top- and backsheets 2, 3 and bonded to respective inner surfaces of these sheets 2, 3.

Referring to FIG. 1, contraction of the elastic members 6, 7, 11 cause a plurality of gathers to be formed along the transversely opposite side edge portions 1a as well as along the longitudinally opposite end portions 1b of the diaper 1 and along the free side edge portions 5b of the leak-barrier sheets 5. In the state of FIG. 1, the diaper 1 is curved in its longitudinal direction with the topsheet 2 inside and the free side edge portions 5b of the leak-barrier sheet 5 rise upward as viewed in FIG. 1 as the elastic members 11 contract.

Figure 4:
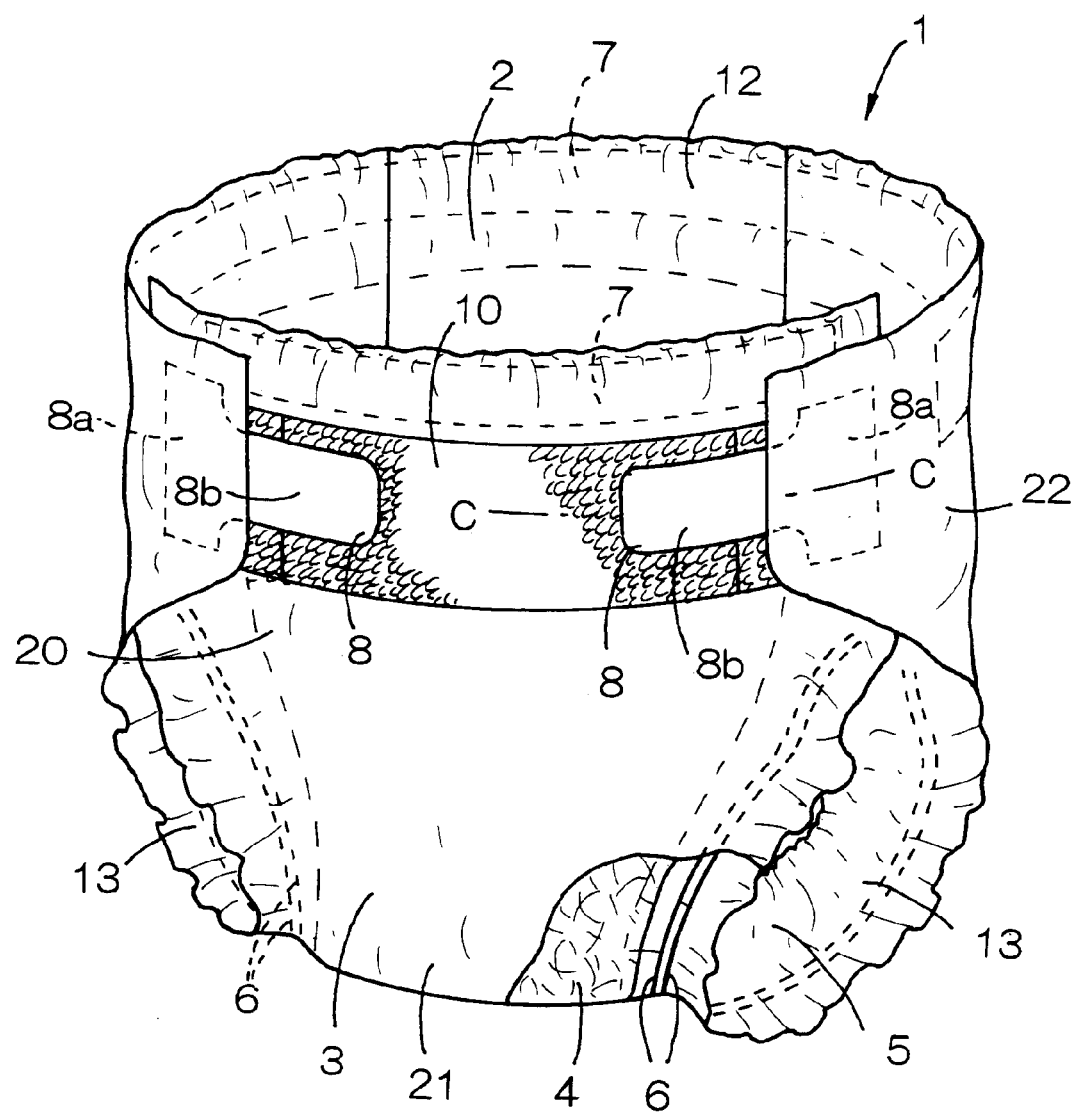
FIG. 4 is a perspective view showing the diaper as its front waist region has been connected to the rear waist region.
Figure 5:
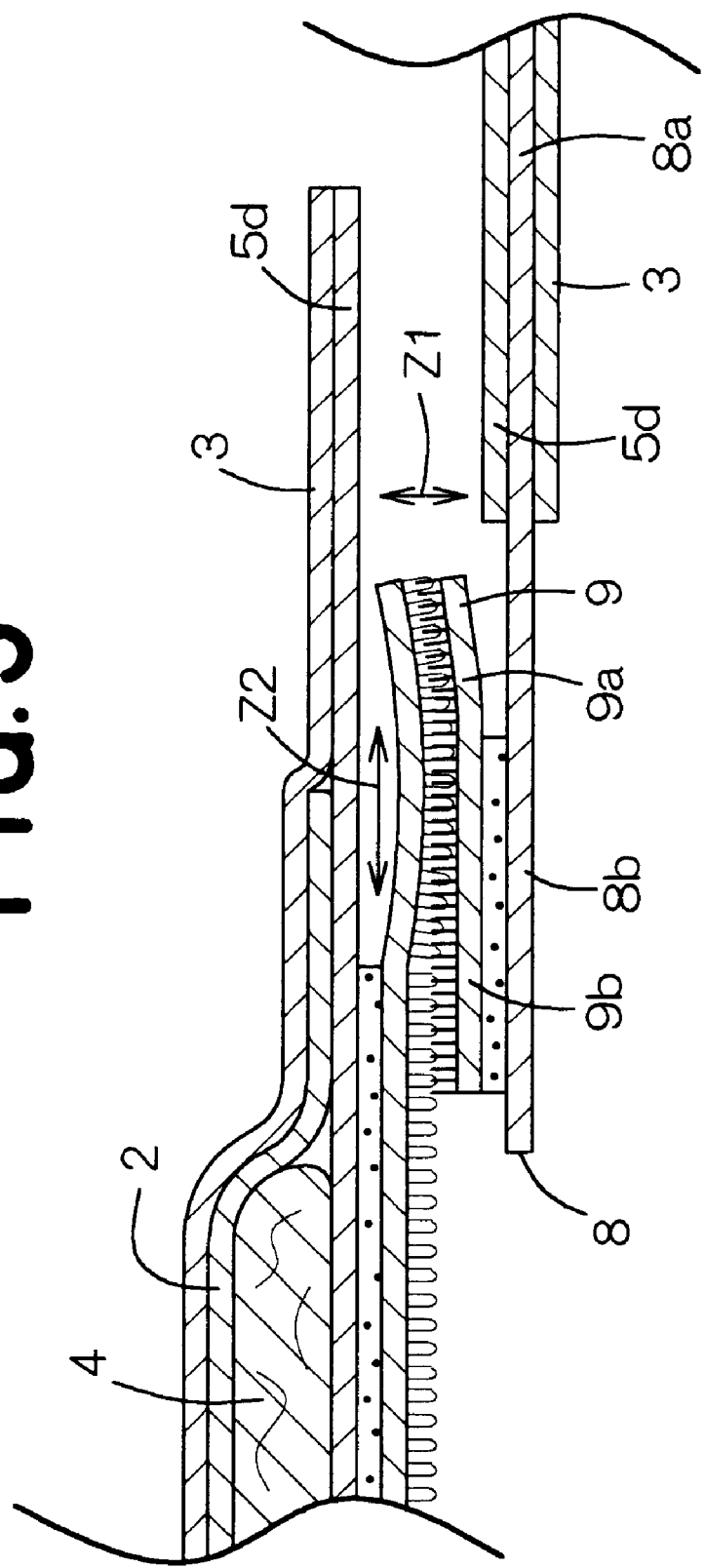
FIG. 5 is a sectional view taken along a line C—C in FIG. 4.

FIG. 4 is a perspective view showing the diaper as its front waist region has been connected to the rear waist region and FIG. 5 is a sectional view taken along a line C—C in FIG. 4. Referring to FIG. 4, the portion of the hook member 9 defined in the vicinity of its inner side 9a is engaged with the portion of the target tape strip 10 extending in its vicinity of the associated side edge 10a. Referring to FIG. 5, a peeling force exerted upon the hook member 9 and the target tape strip 10 is indicated by an arrow Z1 and a shearing force exerted thereupon is indicated by an arrow Z2.

With the diaper 1 actually put on a wearer's body, the tape fasteners 8 are anchored on the outer surface of the target tape strip 10 by means of the hook members 9. More specifically, hooks of the respective hook members 9 are caught by loops of the target tape strip 10 and thereby the hook members 9 are held in engagement with the target tape strip 10. The front and rear waist regions 20, 22 are connected with each other in this manner to define a waist-opening 12 and a pair of leg-openings 13.

The portions of the hook members 9 defined in the vicinity of their inner edges 9a are set free from the respective tape fasteners 8, so these portions of the hook members 9 defined in the vicinity of their inner edges 9a are freely movable without being restrained by the tape fasteners 8. Similarly, the portions of the target tape strip 10 defined in the vicinity of its both side edges 10a are set free from the backsheet 3, so these portions of the target tape strip 10 defined in the vicinity of its both side edges 10a also are freely movable without being restrained by the diaper 1.

With the diaper 1 worn, movement of the wearer's legs may cause the side edge portions 1a of the diaper 1 and, in consequence, a peeling force as well as a shearing force may be exerted upon the hook members 9 and the target tape strip 10. However, the peeling force and shearing force are neither transmitted from the tape fasteners 8 directly to the positions of the respective hook members 9 defined in the vicinity of their inner edges 9a nor directly to the portions of the target tape strip 10 defined in the vicinity of its both side edges 10a. In this way, it is possible for the diaper 1 to prevent the positions of the respective hook members 9 defined in the vicinity of their inner side edges 9a from being readily disengaged from the positions of the target tape strip 10 defined in the vicinity of its both side edges 10a.

Figure 6:
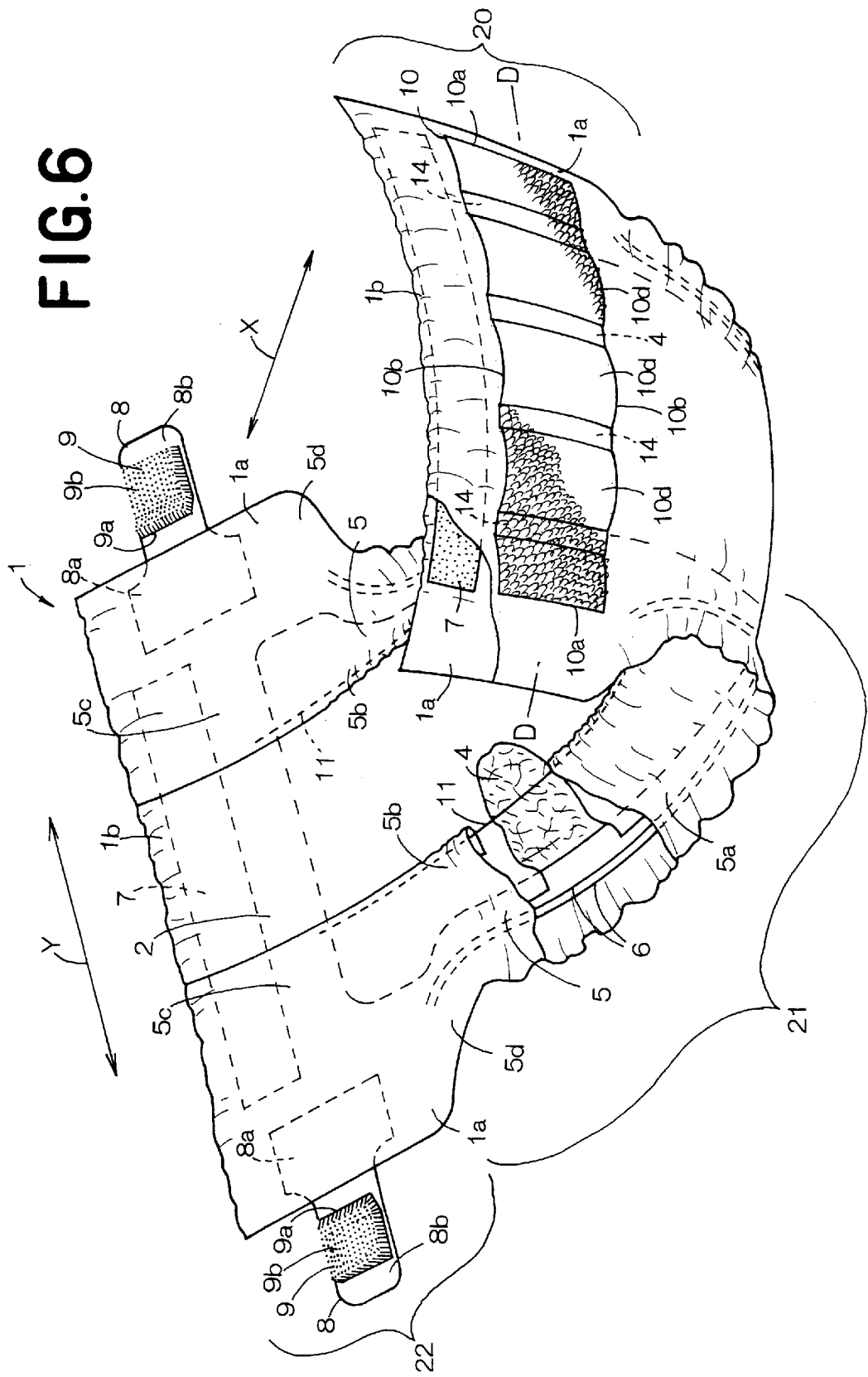
FIG. 6 is a view similar to FIG. 1 but showing the diaper according to an alternative embodiment of this invention.
Figure 7:
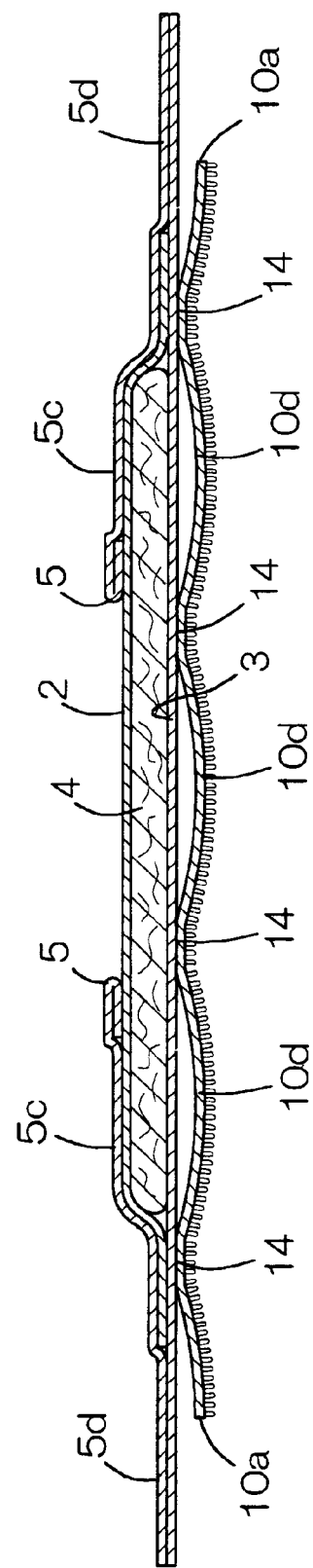
FIG. 7 is a sectional view taken along a line D—D in FIG. 6.

FIG. 6 is a view similar to FIG. 1 but showing the diaper according to an alternative embodiment of this invention and FIG. 7 is a sectional view taken along a line D—D in FIG. 6. The diaper 1 of FIG. 6 is similar to the diaper 1 of FIG. 1 except that the target tape strip 10 is attached to the outer surface of the backsheet 3 along a plurality of bonding zones 14 spaced one from another by a predetermined dimension in the transverse direction. The target tape strip 10 is bonded along these bonding zones 14 to the backsheet 3 by means of adhesive (not shown). Portions of the target tape strip 10 defined in the vicinity of its both side edges 10a are set free from the backsheet 3 and the remaining zones 10d of the target tape strip 10 defined between respective pairs of the adjacent bonding zones 14 are not bonded to the backsheet 3, i.e., set free from the backsheet 3.

In the case of the diaper 1 according to this alternative embodiment, the target tape strip 10 is movable relatively to the diaper 1 not only in its portions defined in the vicinity of its both side edges 10a but also in the zones 10d, so there is no anxiety that the peeling force as well as the shearing force might be transmitted directly to the zones 10d. Accordingly, even if the portions of the hook members 9 defined in the vicinity of their inner side edges 9a come in engagement with the zones 10d of the target tape strip 10, it is not apprehended that the portions of the hook members 9 defined in the vicinity of their inner side edges 9a might be readily disengaged from the zones 10d of the target tape strip 10.

The top sheet 2 may be formed from a liquid-pervious sheet such as a nonwoven fabric or a porous plastic film, more preferably from a liquid-pervious and hydrophilic sheet. The backsheet 3 may be formed from hydrophobic nonwoven fabric, liquid-impervious plastic film or a laminated sheet consisting of a hydrophobic nonwoven fabric and a plastic film, more preferably from a breathable and liquid-impervious sheet. It is also possible to form the backsheet 3 from a composite nonwoven fabric comprising a highly water-resistant and a flexible melt blown nonwoven fabric and two layers of a spun bond nonwoven fabric sandwiching the melt blown nonwoven fabric therebetween.

The nonwoven fabric used for this invention may be of various types such as spun lace-, needle punch-, melt blown-, thermal bond-, spun bond-, chemical bond- and air through-types. The component fiber of the nonwoven fabric may be selected from a group including polyolefine-, polyester- and polyamide-based fibers and core-sheath-type or side-by-side-type polyethylene/polypropylene or polyester conjugated fibers.

The core 4 comprises a mixture of fluff pulp, high absorption polymer particles and thermoplastic synthetic resin fiber compressed to a desired thickness. The high absorption polymer may be selected from a group including graft polymer of starch-based, modified cellulose-based and synthetic polymers.

Bonding the top- and backsheets 2, 3 to each other, bonding of the core 4 to the top- and backsheets 2, 3, and attaching of the elastic members 6, 7, 11, the tape fasteners 8 and the target tape strip 10 may be carried out by means of any suitable adhesive such as a hot melt adhesive or using a suitable welding technique such as a heat sealing or a supersonic sealing technique.

With the disposable diaper according to this invention, the portions of the respective hook members defined in their inner side edges are freely movable relatively to the diaper since the portions are set free from the respective tape fasteners. With this diaper actually put on the wearer's body, even if a peeling force and/or a shearing force tending to disengage the hook members from the target tape strip are exerted upon the hook members and the target tape strip, such peeling force and/or shearing force are not transmitted directly to the portions of the hook members, so it is not apprehended that the portions of the hook members defined in the vicinity of their inner side edges might be readily disengaged from the target tape strip.

In the embodiment of this invention so arranged that the portions of the target tape strip defined in its both side edges are set free from the backsheet, the portions of the target tape strip defined in the vicinity of its both side edges are freely movable without being restrained by the diaper. With this embodiment, even if the respective hook members are engaged with the portions of the target tape strip defined in the vicinity of its both side edges, there is no anxiety that the hook members might be easily disengaged from the target tape strip since the peeling force and/or the shearing force are not transmitted from the diaper directly to the portions of the target tape strip defined in the vicinity of its both side edges.

In the embodiment of the diaper according to this invention having the target tape strip attached to the outer surface of the backsheet along a plurality of bonding zones spaced one from another by a predetermined dimension in the transverse direction, the zones defined between respective pairs of the adjacent bonding zones are set free from the backsheet, so these not bonded zones are freely movable without being restrained by the diaper. Even if the hook members come in engagement with the free zones, there is no apprehension that the hook members might be readily disengaged from the target tape strip since the peeling force and/or the shearing force are not transmitted from the diaper directly to the free zones of the target tape strip.

What is claimed is:

1. A disposable diaper comprising:

a liquid-pervious topsheet;

a liquid-impervious backsheet;

a liquid-absorbent core disposed between said liquid-pervious topsheet and said liquid-impervious backsheet;

a front waist region;

a rear waist region;

a crotch region extending between said front waist region and said rear waist region;

a pair of tape fasteners for connecting said front and rear waist regions to each other, said pair of tape fasteners extending outward from transversely opposite side edge portions of said rear waist region in a transverse direction and comprising an intermediate base portion; and a target tape strip for anchoring said pair of tape fasteners thereon, said target tape strip being provided on an outer surface of the backsheet in said front waist region, one of a plurality of hook members and a plurality of loop members provided on an entire surface of said intermediate base layer of each of said tape fasteners which surface faces said target tape strip, an inner edge portion of said intermediate base layer of each of said tape fasteners lying in a vicinity of an associated side edge portion of said rear waist region is unattached from any underlying structure and said target tape strip comprising another of said hook member and said loop member.

2. The diaper according to claim 1, wherein opposite side edge portions of said target tape strip which lie in a vicinity of the transversely opposite side edge portions of said front waist region are unattached to said backsheet.

3. The diaper according to claim 2, wherein said target tape strip is bonded to said backsheet along a plurality of bonding zones spaced apart from one another in the transverse direction and remaining zones defined between adjacent one of said bonding zones are unattached to said backsheet.

* * * * *